US011344308B2

(12) United States Patent
Hernandez et al.

(10) Patent No.: US 11,344,308 B2
(45) Date of Patent: May 31, 2022

(54) MODULAR MAGNETIC DEVICES FOR USE IN CREATING TISSUE ANASTOMOSIS

(71) Applicant: IRCAD, Strasbourg (FR)

(72) Inventors: Juan Hernandez, Strasbourg (FR); Michele Diana, Savigny (CH); James Kennedy Wall, Palo Alto, CA (US)

(73) Assignee: IRCAD, Strasbourg (FR)

( * ) Notice: Subject to any disclaimer, the term of this patent is extended or adjusted under 35 U.S.C. 154(b) by 60 days.

(21) Appl. No.: 16/717,915

(22) Filed: Dec. 17, 2019

(65) Prior Publication Data

US 2020/0187947 A1    Jun. 18, 2020

Related U.S. Application Data

(63) Continuation of application No. 14/237,521, filed as application No. PCT/US2012/046272 on Jul. 11, 2012, now Pat. No. 10,568,630.

(60) Provisional application No. 61/506,710, filed on Jul. 12, 2011.

(51) Int. Cl.
*A61B 17/11* (2006.01)
*A61B 17/00* (2006.01)

(52) U.S. Cl.
CPC .......... *A61B 17/1114* (2013.01); *A61B 17/11* (2013.01); *A61B 2017/00292* (2013.01); *A61B 2017/00862* (2013.01); *A61B 2017/00876* (2013.01); *A61B 2017/1117* (2013.01); *A61B 2017/1132* (2013.01); *A61B 2017/1135* (2013.01); *A61B 2017/1139* (2013.01)

(58) Field of Classification Search
CPC ................ A61B 17/11; A61B 17/1114; A61B 2017/00292; A61B 2017/00862; A61B 2017/00876; A61B 2017/1117; A61B 2017/1132; A61B 2017/1135; A61B 2017/1139

See application file for complete search history.

(56) References Cited

U.S. PATENT DOCUMENTS

| 4,197,840 A | 4/1980 | Beck et al. |
| 5,891,159 A | 4/1999 | Sherman et al. |
| 6,110,187 A | 8/2000 | Donlon |
| 6,352,543 B1 | 3/2002 | Cole |
| 8,092,378 B2 | 1/2012 | Roth et al. |

(Continued)

FOREIGN PATENT DOCUMENTS

| CN | 1582857 A | 2/2005 |
| EP | 2086426 A2 | 8/2009 |

(Continued)

OTHER PUBLICATIONS

Brazilian Patent Application No. BR112014000655-5 Office Action dated Oct. 29, 2019.

(Continued)

*Primary Examiner* — Bernard Rojas
(74) *Attorney, Agent, or Firm* — Wilson Sonsini Goodrich & Rosati (57) ABSTRACT

The present disclosure provides modular magnetic anastomosis devices that can be implemented in digestive surgery or in any circumstance of anastomosis between adjacent organs or two hollow viscera. The device is minimally invasive and easily and quickly delivered using laparoscopic or endoscopic procedures.

15 Claims, 6 Drawing Sheets

(56) References Cited

U.S. PATENT DOCUMENTS

| | | | |
|---|---|---|---|
| 2002/0147385 A1 | 10/2002 | Butler et al. | |
| 2005/0283235 A1 | 12/2005 | Kugler et al. | |
| 2007/0276378 A1 | 11/2007 | Harrison et al. | |
| 2008/0161644 A1 | 7/2008 | Ghabrial | |
| 2009/0125042 A1 | 5/2009 | Mouw | |
| 2010/0076573 A1 | 3/2010 | Kugler et al. | |
| 2011/0160752 A1 | 6/2011 | Aguirre | |
| 2011/0295285 A1* | 12/2011 | McWeeney | A61B 17/11 606/153 |
| 2012/0197062 A1 | 8/2012 | Requarth | |
| 2013/0253550 A1 | 9/2013 | Beisel et al. | |
| 2015/0164508 A1 | 6/2015 | Hernandez et al. | |
| 2015/0342608 A1 | 12/2015 | Hernandez | |
| 2016/0022266 A1 | 1/2016 | Lukin et al. | |
| 2016/0262761 A1 | 9/2016 | Beisel et al. | |
| 2019/0274687 A1* | 9/2019 | Wang | A61B 17/1114 |

FOREIGN PATENT DOCUMENTS

| | | | |
|---|---|---|---|
| EP | 2934347 A2 | 10/2015 | |
| JP | 2006271832 A | 10/2006 | |
| JP | 4681920 B2 | 5/2011 | |
| SU | 736966 A1 | 5/1980 | |
| WO | WO-9802099 A1 | 1/1998 | |
| WO | WO-2004096013 A2 | 11/2004 | |
| WO | WO-2009048954 A1 | 4/2009 | |
| WO | WO-2014102621 A2 | 7/2014 | |

OTHER PUBLICATIONS

Chinese Patent Application No. 201280040553.9 Office Action dated Oct. 29, 2015.
Chinese Patent Application No. 201280040553.9 Second Office Action dated Sep. 20, 2016.
EP Patent Application No. 12811240.6 Extended European Search Report dated Jun. 9, 2015.
European Patent Application No. 19174351.7 Extended European Search Report dated Jul. 18, 2019.
International Search Report and Written Opinion for PCT Patent Application No. PCT/US2012/046272 dated Oct. 1, 2012.
"Jamshidi et al., Magnamosis: Magnetic compression anastomosis with comparison to suture and staple techniques. J.Pediatr. Surg., 44(1):222-228 (2009)".
"PCT Patent Application No. PCT/IB2013/003246 International Preliminary Report on Patentability dated Jul. 2, 2015".
PCT/IB2013/003246 International Search Report and Written Opinion dated Feb. 5, 2015.
ROC (Taiwan) Patent Application No. 102147684 Office Action and Search Report dated Nov. 18, 2015.
Taiwan Patent Application No. 105126839 Office Action dated May 1, 2017.
U.S. Appl. No. 14/237,521 Final Office Action dated Mar. 7, 2019.
U.S. Appl. No. 14/237,521 Office Action dated Dec. 1, 2016.
U.S. Appl. No. 14/237,521 Office Action dated Jun. 14, 2016.
U.S. Appl. No. 14/237,521 Office Action dated Jun. 16, 2017.
U.S. Appl. No. 14/237,521 Office Action dated May 10, 2018.
U.S. Appl. No. 14/237,521 Office Action dated Sep. 29, 2015.
U.S. Appl. No. 14/654,643 Office Action dated Jan. 17, 2017.

* cited by examiner

Modular Magnetic Anastomosis Device : Example 1

Modular Magnetic Anastomosis Device : Example 2

Modular Magnetic Anastomosis Device : Example 3

Modular Magnetic Anastomosis Device : Example 4

Modular Magnetic Anastomosis Device : Example 5

Different geometrical structure (magnet with resilient material jacket).

Fig. 26

MODULAR MAGNETIC DEVICES FOR USE IN CREATING TISSUE ANASTOMOSIS

CROSS-REFERENCE

This application is a continuation of U.S. application Ser. No. 14/237,521, filed Jun. 23, 2014, which is a national stage entry of International Application No. PCT/US2012/046272, filed Jul. 11, 2012, which claims priority to U.S. Provisional Application No. 61/506,710, filed Jul. 12, 2011, each of which is entirely incorporated herein by reference.

BACKGROUND

The present invention relates to a modular magnetic anastomosis device for a gastro-intestinal procedure or circumstance where anastomosis between two hollow organs is required in a minimally invasive surgery procedure.

SUMMARY

The present invention extends this concept by means of implementing a modular magnetic anastomosis device that can be implemented in digestive surgery or in any circumstance of anastomosis between adjacent organs or two hollow viscera.

In one embodiment the modular magnetic assembly possesses the non-deployed configuration and can be placed in a small sized channel and can be used in laparoscopy and endoscopy known to the person skilled in the art. The modular magnetic assembly takes the deployed form at its implementation position.

In another embodiment the modular assembly anastomosis device is flexible and the modular aspect of the device allows it to be available in different sizes by addition of magnetic elements and adapts to the anatomical shape of the structure in which it is to be implemented.

In one embodiment the anastomosis device is linear.

In another embodiment the anastomosis device can be U-shaped in its deployed configuration.

Alternatively the anastomosis device can be S-shaped in its deployed configuration.

In another embodiment the device has a circular deployed configuration.

According to one embodiment the modular magnetic anastomosis device is a set of magnetic components, the two sets form the device used for forming an anastomosis between two bodily walls.

In another embodiment the modular magnetic set is enveloped in a jacket of resilient material.

Alternatively the modular magnetic component is enveloped in a jacket of biodegradable material.

In an alternative embodiment the magnets are embedded in a biodegradable material.

In one embodiment self assembly in a connected chain of magnetic components in this modular device is based on an even number of magnetic dipoles with alternate North-South/South-North orientation.

In another embodiment alternate geometrical flexible materials are connected to the magnet and allow for mechanical articulation of the magnets.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The accompanying drawings incorporated in and forming a part of the specification illustrate several aspects of the present invention and together with the description serve to explain the principles of the invention. In the drawings.

DETAILED DESCRIPTION

In creating the anastomosis in the digestive tract several methods have been developed with different techniques and instrumentation, such as manual and mechanical sutures using staplers, biological glue or through compression.

The circular stapler (EEA) allows to perform complex procedures such as colic resections or gastric bypasses via a minimally invasive approach (laparoscopic). However, the rigid structure of circular stapler does not allow anastomosis beyond the rectum. Also, using the circular stapler during a gastric bypass needs an enlarged incision through one of the operating trocars.

Anastomosis through compression is a concept initially described by Denan in 1826 and was later popularized by Murphy in 1892 with the "Murphy Button". It is a surgical procedure that needs introduction of two metallic rings, screwed one against the other in order to generate a constant compression force on intercalated tissues. This procedure induces secondary health issues after the anastomosis trough the ischemia→necrosis→cicatrizing cycle.

Covidien recently has developed Valtrac™, a set of biofragmentable rings (Covidien, Norwalk Conn.) which are composed of two rings made of absorbable material, this device eliminate manual or mechanic suture while maintaining a comparable dehiscence and stenosis rate.

Experimentations with magnetic anastomosis in surgery date back to the 1980s by a Dutch group which also used magnetic rings to perform muco-mucosal anastomosis while the serous membrane (serosa) had to be sutured by hand. The latency between the positioning of magnets and the realization of the anastomosis took 7 to 12 days. This prolonged time to obtain anastomosis ended the later development of the device.

A device, called MAGNAMOSIS™, is composed of 2 magnetic rings, auto-oriented, producing a compression force with a progressive internal-external gradient. This device has been developed by the research group of Prof. Harrison from the University of San Francisco (Calif.).

Detailed embodiments of the present invention are disclosed herein. The present invention comprises a modular magnetic device that is minimally invasive, easily and quickly delivered and is accurately positioned via laparoscopy or endoscopy, without the use of the staples.

According to one embodiment constructed with the teaching of the present invention, a magnetic anastomosis device used for forming an anastomosis between two bodily walls includes a first magnet assembly and a second magnet assembly configured to be magnetically coupled to compress the two bodily walls therebetween to form the anastomosis. The magnet assembly of the present invention is a modular magnetic structure with variable geometry. The articulated flexible modular device is composed of a network of magnetic elements placed and maintained in place by a flexible material made of resilient, biocompatible material and shape memory material or a material coated with a biocompatible material, known to a person skilled in the art. Suitable resilient materials include metal (e.g. stainless steel), alloys (e.g. nickel titanium) or polymers (e.g. polyethylene, polytetrafluoroethylene (PTFE) including Teflon®, polyvinyl chloride (PVC), and composites.

It will be recognized by those skilled in the art that the elongate modular magnet assemblies of the present invention are capable of being delivered with the same small delivery configuration as prior art, but also provide the advantage of reducing the probability of the anastomosis being closed over time and eliminating the need to intervene the patient for a second procedure to place a stent in the anastomosis to prevent closure thereof. Moreover, those skilled in the art will recognize the centering and alignment advantages of having two magnets disposed within each of the respective magnet assemblies.

Accordingly, it will be recognized by those skilled in the art that the modular magnetic assembly with a smaller delivery configuration may be easily located within the body for accurate delivery using laparoscopic trocars through single skin incision. The catheter made of non-ferromagnetic material can deliver the two sets of magnets. The placing step preferably includes introducing the first set of modular anastomosis device into one of the viscera and positioning the set of magnet assemblies with the wire guide that help the device acquire the deployed configuration. After delivery of first set of the magnets to the location to be deployed by retracting the wire guide, the delivery portion of the catheter can then be positioned and deliver the second set of the magnet assembly to the second deployment position and the wire guide can be retracted.

The excising step includes introducing a cutting instrument into one of the viscera and manipulating the cutting instrument.

The two sets of magnet assemblies can be maneuvered to mate one another; once mated, the ischemic necrosis process can begin on the walls of the two viscera being treated.

Alternatively, the set of the magnets may also be implanted non-surgically using endoscopy where one or more catheters are introduced into the stomach cavity via the patient's mouth and esophagus and colon.

It will be recognized by those skilled in the art than the modular magnet assemblies can pass through the body naturally or can be removed by means such as laparoscopic removal, endoscopic removal or other procedure.

Figure 17:
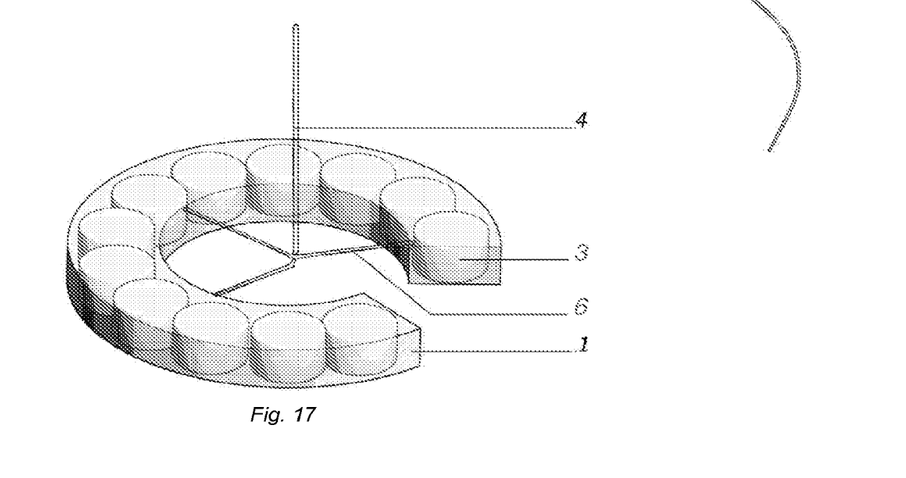
FIG. 17 is a presentation of simple magnets and external jacket.

Accordingly, it will be recognized by those skilled in the art that the modular magnetic assembly in its non-deployed form can be linear. This particularity allows the use of a small sized channel for implementation of the modular magnetic device. The modular magnetic assembly possesses the advantage to be deployed in an open structure, thus permitting adaptation of the anastomosis device to anatomical features. The modular magnet assembly in the deployed configuration can take different shapes; such as circular, elongated, U shape and S shape The concept of magnet self assembly in a connected chain of magnetic components in this modular device is based on an even number of magnetic dipoles with alternate North-South/South-North orientation. One example of this alternate orientation is shown in FIG. 17 where a first magnet has a North (5A)-South (5(B) orientation and a second adjacent magnet has a South (5C)-North (5D) orientation. This alternate orientation of the magnets confers stability of the magnets and global magnetic inertia in the magnetic chain. However, despite the magnetic inertia of one part of the modular anastomosis device, in presence of each other the set of the magnets auto-orient and form the anastomosis set.

Although, only one set of magnetic assembly will be described, two magnet assemblies are intended for use as a magnetic anastomosis device.

Example 1

Set of magnets enveloped in a resilient material with a hole for introduction of the wire guide, which will enter into the passageway created in the flexible material of the neck and will allow passage from no-deployed to deployed configuration. FIG. 1 to FIG. 11 describe this example.

Figures 1, 2:
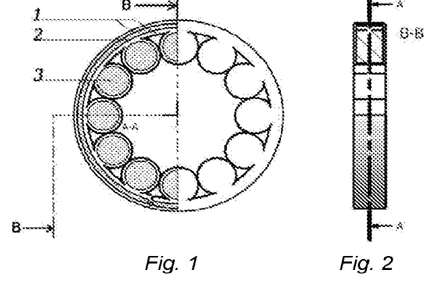
FIG. 1 depicts how each set is formed of a chain of magnets (3), a neck comprised of flexible material (2), the resilient material (2) allows to the chain of the magnets to adopt a round structure after deployment and a jacket made of resilient material with a low friction coefficient allowing the easy movement of the device during an operation.
FIG. 2 is a cross sectional view of the magnet chain of example 1.
Figure 3:
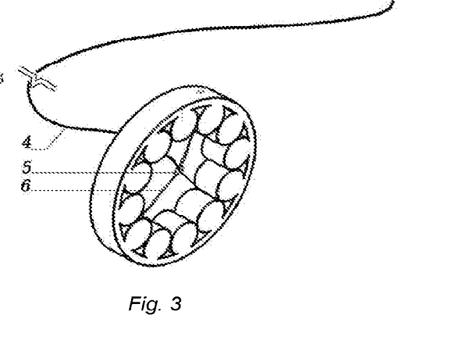
FIG. 3 illustrates the deployed form of the magnet with wire guides.
Figure 4:
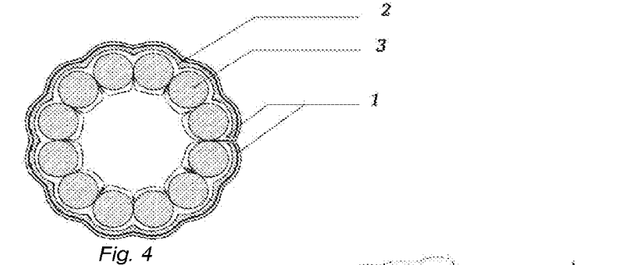
FIG. 4 shows a variant of the magnet set.
Figure 5:
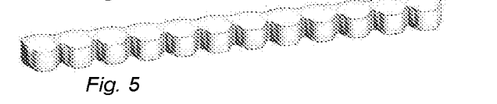
FIG. 5 to FIG. 9 illustrate the transition from the non-deployed linear form to the deployed circular structure of the device.
Figures 6, 7:
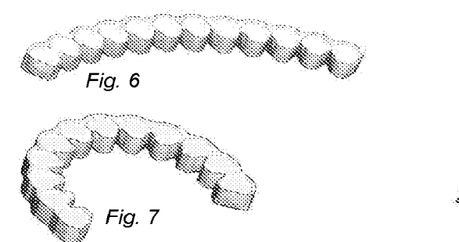
Figure 8:
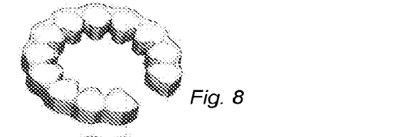
Figure 9:
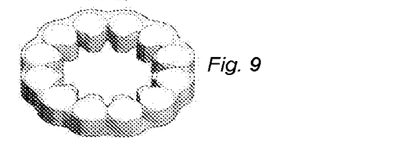

As illustrated in FIG. 1, each set is formed of a chain of individual magnets (3), a neck comprised of flexible material (2), the resilient material (2) allows to the chain of the magnets to adopt a round structure after deployment and a jacket made of resilient material with a low friction coefficient allowing the easy movement of the device during an operation. The variant in FIG. 4 has the same structural feature with a more flexible jacket enveloping the magnets.

FIG. 5 to FIG. 9 show the transition from a non-deployed linear to one of deployed circular form.

Figure 10:
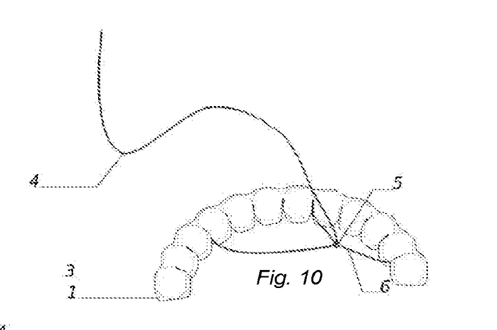
FIG. 10 is the transition of the non deployed form of the magnet with the wire guide.
Figure 11:
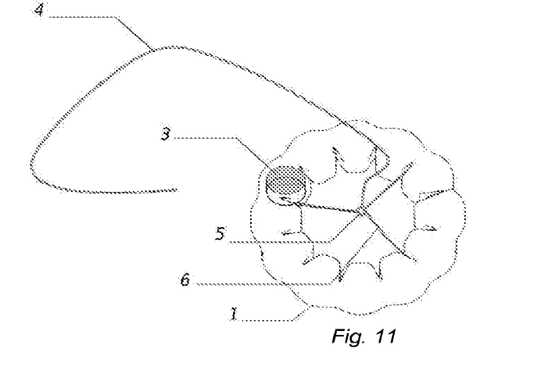
FIG. 11 is the magnet in deployed form with the wire guides.

The illustrations in FIGS. 10 and 11 describe the passage of the non-deployed to circular deployed form of the wire guide assembly of the magnet after delivery to the organ where it is to be implemented. The wire-guide (4) and (6) positions the magnetic chain and brings the terminal parts of the magnetic chain into proximity and aids, by mutual attraction of the magnets, in the closure of the ring; the deployed form and (5) is the central crossing ring for the wire guide.

Example 2

Figure 12:
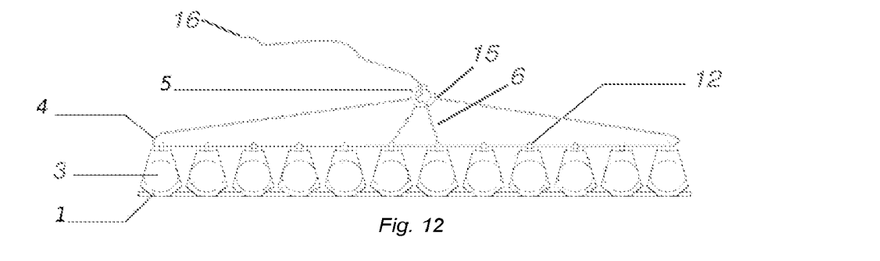
FIG. 12 is a representation of the encapsulated shell attached to a flexible band of example 2.
Figure 13:
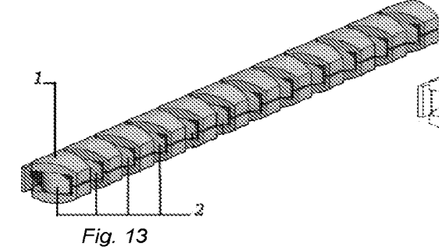
FIG. 13 illustrates detailed cross-representation of the assembled shell of the device of example 2.
Figure 14:
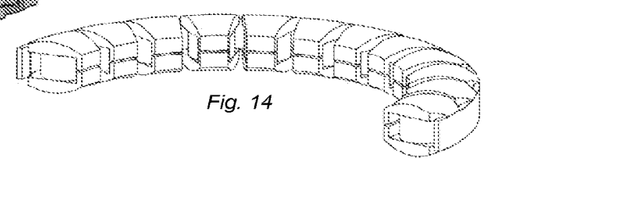
FIG. 14 depicts a cross-sectional view of the magnet assembly for the device of example 2.
Figure 15:
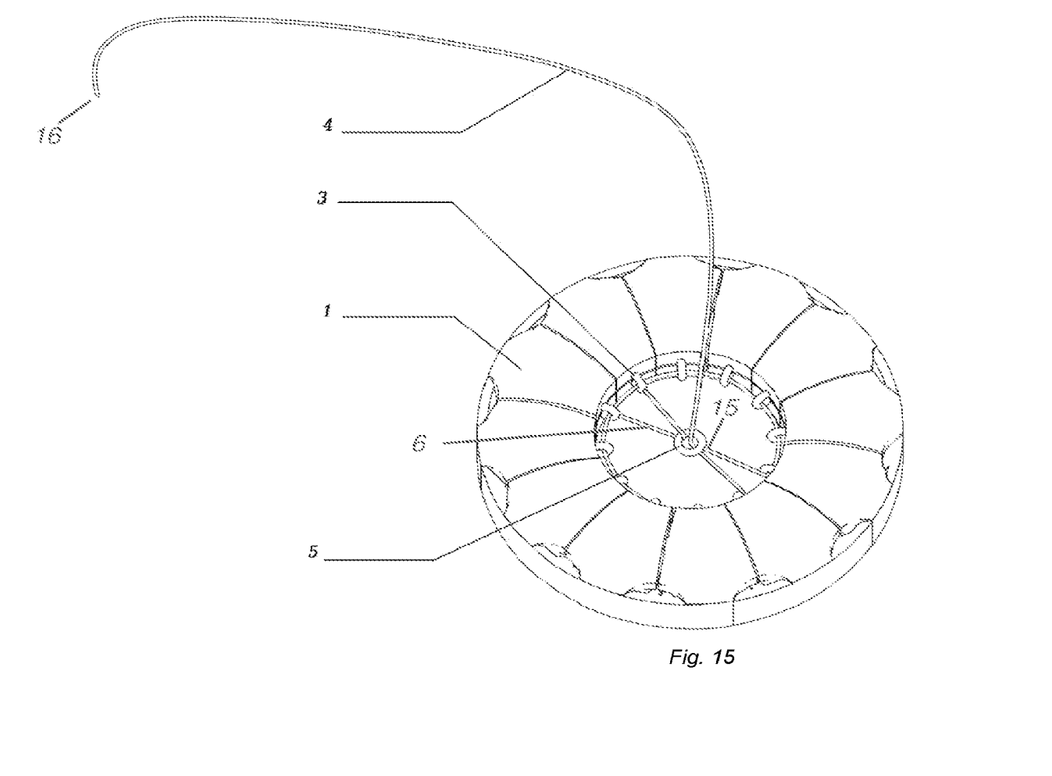
FIG. 15 illustrates the deployed structure of the magnet assembly.
Figure 23:
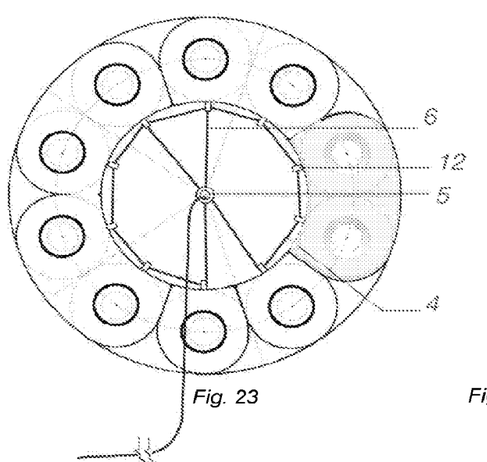
FIG. 23 is a cross-sectional view of the magnet assemblies.

FIG. 12 to FIG. 15 illustrate the modular magnetic assembly as a chain formed from separate encapsulated magnets and FIGS. 12 and 15 include all of the features illustrated by FIGS. 10, 11, and 23. Every magnet (3) is separately enveloped in a shell of a resilient or biocompatible material (2) and affixed to a flexible band that can adopt its deployed shape after being deployed in the organ to where it is to be implemented. A passageway created between shells formed by a plurality of ring structures (12) allows the attachment of a first wire guide (4), the first wire guide (4) having a first end (15) and a second end (16). FIG. 12 to FIG. 14 presents the organization of such a modular magnetic assembly. FIG. 15 is a representation where first and second wire guides (4) and (6) enter the central ring (5) and close the device to its deployed form. As shown in FIGS. 12 and 15, in this embodiment, the second wire guide (6) couples the central ring (5) to the modular magnetic assembly.

FIG. 14 and FIG. 15, illustrate the biconvex structure of the magnet set. The biconvex structure refines the quality of the magnetic compression anastomosis.

Example 3

Figure 16:
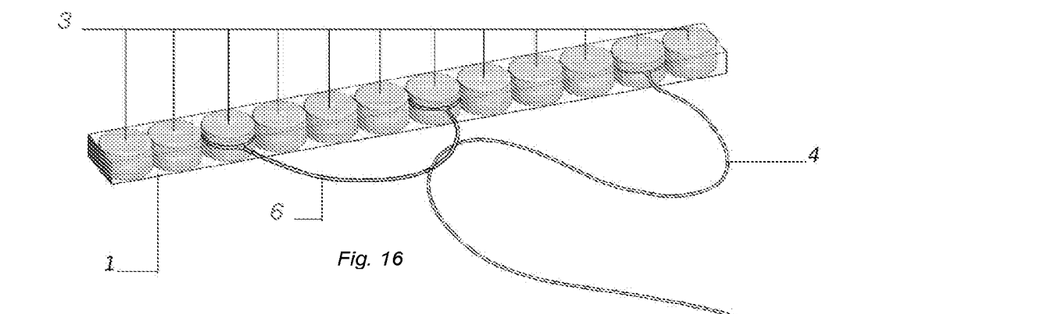
FIG. 16 illustrates the structure of a set of the modular magnet assembly for a device of example 3.
Figure 18:
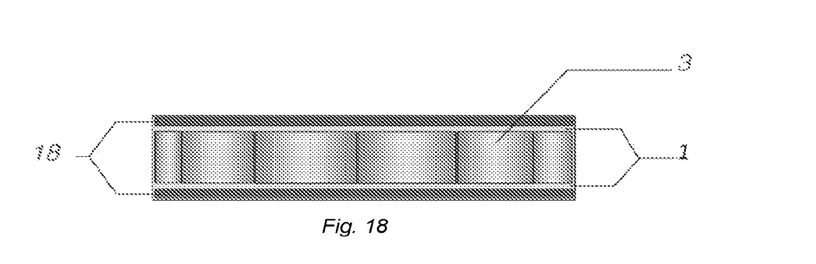
FIG. 18 is a profile view of the set of the magnets of example 3.

FIG. 16, 17, 18 describe the device of Example 3. In one embodiment of this invention the magnet network is embedded in layers of resilient material. This laminated structure is compromised of a silicon layer (1) around the magnet (3) and a rubber layer (18) covering the silicon. In its delivery form the magnet assembly is in a linear structure. In addition of this organization, the chain of the magnet can be enveloped in a jacket of resilient and biocompatible material.

FIGS. 16 and 17 illustrate the structure of one set of the magnets.

FIG. 17 is a presentation of simple magnets and external jacket.

FIG. 18 is a profile view of the set of the magnets, where (2) is the magnet, (1) the silicon layer and (18) the biocompatible polymer.

Example 4

Figure 19:
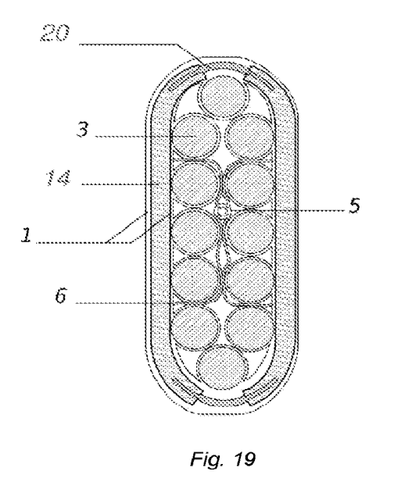
FIG. 19 illustrates the non-deployed form of the magnet assembly of example 4.
Figure 20:
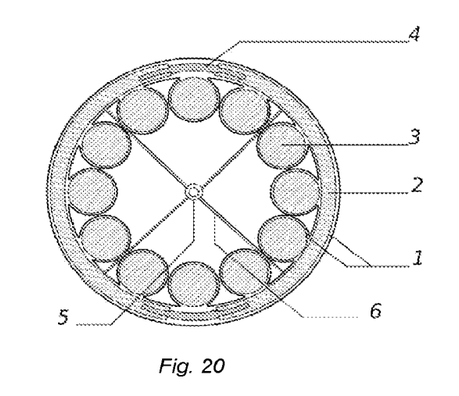
FIG. 20 describes the deployed form of example 4.

FIG. 19 and FIG. 20 describe the non-deployed and deployed form of the magnet assembly representing another example of this invention compromises a set of magnets encapsulated in a resilient or biocompatible material which may also be a shape memory material allowing the delivery of magnets in a flattened configuration. A spring (20) of resilient or biocompatible material is on either side of the device in the non-deployed configuration. When it is delivered the magnet assembly will automatically assume its deployed configuration.

The biodegradable resilient material (2) envelopes magnets (3) and the shape memory material (14). The central circular ring (5) holds the wire guides (6).

Example 5

FIG. 21 to FIG. 25 describe different elements of the modular magnetic assembly of example 5.

According to this example in accordance with the teachings of the present invention the modular magnet assembly is composed of a chain of ring-shaped magnetic elements formed from a plurality of individual magnets (3) linked to each other by a network of articulate mechanic elements (1 and 2). The ring-shaped magnets are enveloped with a network of sheets that allows the device to pass from a non-deployed structure to the deployed structure. Alternate and specific geometry of the sheets is designed for the ease of the articulation between magnets in the chain.

Figure 25:
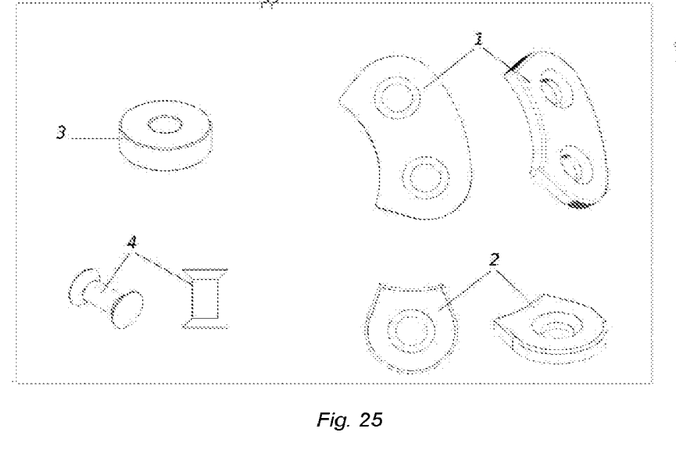
FIG. 25 describes different components of the magnet.
Figure 26:
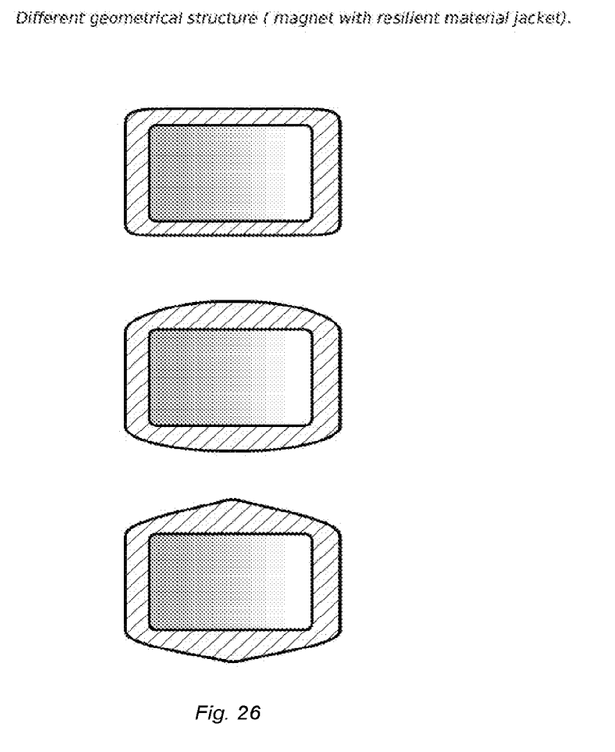
FIG. 26 presents different geometrical structure of magnet and resilient material jacket.

The individual magnets and the sheets are linked together through a centralized axis (22).

Figure 21:
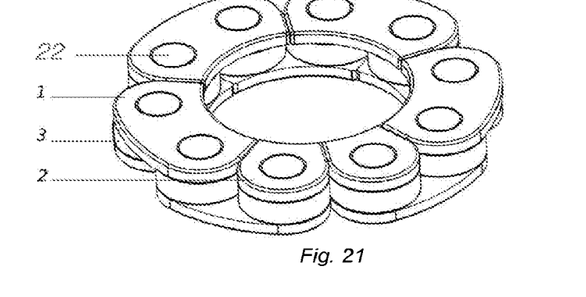
FIG. 21 illustrates the ring shaped modular magnetic anastomosis device in the deployed configuration of example 5.

FIG. 21 illustrates the ring shaped modular magnetic anastomosis device in the deployed configuration.

Figure 22:
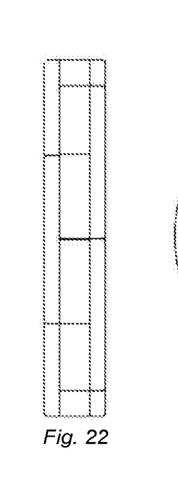
FIG. 22 shows a profile view of the device.

FIG. 22 shows a profile view of the device.

FIG. 23 is a cross-sectional view of the magnet assemblies; illustrate the passageway formed with the ring structure (12) for the wire guide (4). The central ring (5) is used for the wire guide (6).

Figure 24:
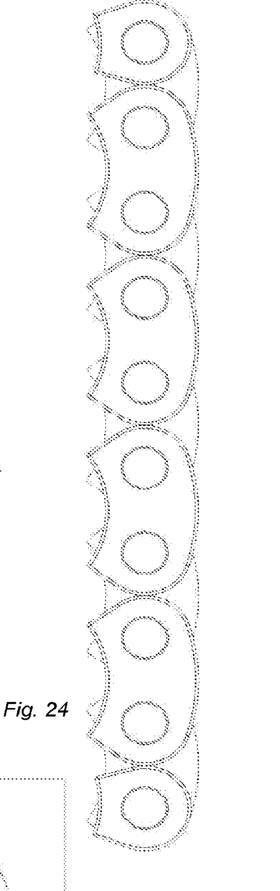
FIG. 24 illustrates the linear non deployed configuration.

FIG. 24 illustrates the linear non deployed configuration.

FIG. 25 describes different components of the magnet, flexible structured sheets in the various geometries (1 and 2); the magnet (3) and the component forming the central axis linking the sheets and the magnetized rings.

What is claimed is:

1. A modular magnet assembly for anastomosing tissue comprising:
    a) a first set of modular magnets; and
    b) a second set of modular magnets;
    wherein the first set of modular magnets and the second set of modular magnets are configured for placement on a first body wall and a second body wall respectively, within such a distance that the first set of modular magnets and the second set of modular magnets are magnetically attracted to one another through a defined tissue area, and are further configured to magnetically couple such that a magnetic coupling of the first set of modular magnets with the second set of modular magnets compresses the first body wall and the second body wall between the magnetically coupled first set of modular magnets and second set of modular magnets to form an anastomosis between the first body wall and the second body wall;
    characterized in that the magnets of the first set of modular magnets are positioned so that an even number of dipoles of the magnets of the first set of modular magnets have an alternate north-south, south-north orientation.

2. The modular magnet assembly of claim 1, wherein
    (i) the first set of modular magnets and the second set of modular magnets comprise at least 2 magnets;
    (ii) the first set of modular magnets and the second set of modular magnets have a delivery configuration; or
    (iii) the first set of modular magnets and the second set of modular magnets have a deployment configuration.

3. The modular magnet assembly of claim 2(iii), wherein
    (i) the deployment configuration is a circular shape;
    (ii) the deployment configuration is an elongated shape;
    (iii) the deployment configuration is a U shape;
    (iv) the deployment configuration is an S shape; or (v) further comprising a wire guide configured to switch a configuration of each of the first and second sets of modular magnets from a delivery configuration to the deployment configuration.

4. The modular magnet assembly of claim 1, wherein each of the first set of modular magnets and the second set of modular magnets comprises:
   a) a chain of magnets,
   b) a neck composed of flexible material with a passageway sized to receive a wire guide,
   c) a jacket composed of a resilient material with a hole used as the wire guide.

5. The modular magnet assembly of claim 4, wherein
   (i) a delivery configuration of the modular magnet assembly is an elongated shape; or
   (ii) a deployment configuration of the modular magnet assembly is selected from the group consisting of:
      a) a circular shape;
      b) a U shape;
      c) an S shape; and
      d) an elongated shape.

6. The modular magnet assembly of claim 1, wherein each magnet of the first set of modular magnets and the second set of modular magnets is separately enveloped in a shell.

7. The modular magnet assembly of claim 6, wherein
   (i) the shell is a resilient material;
   (ii) the shell is a biocompatible material;
   (iii) the encapsulated shell is affixed to a flexible band;
   (iv) encapsulated shells are joined with a wire guide;
   (v) a delivery configuration of the modular magnet assembly is an elongated shape;
   (vi) a deployment configuration of the modular magnet assembly is selected from the group consisting of:
      a) a circular shape;
      b) a U shape;
      c) an S shape; and
      d) an elongated shape; or
   (vii) the circular deployment configuration is biconvex.

8. The modular magnet assembly of claim 1, wherein the modular magnet assembly is embedded in a multilayer structure, wherein the multilayer structure comprises:
   a) a rubber layer;
   b) a silicon layer;
   c) magnets.

9. The modular magnet assembly of claim 8, wherein
   (i) the multilayer structure is enveloped in a jacket of resilient material;
   (ii) the multilayer structure is enveloped in a jacket of biocompatible material;
   (iii) a delivery configuration of the modular magnet assembly is an elongated shape; or
   (iv) a deployment configuration of the modular magnet assembly is selected from the group consisting of:
      a) a circular shape;
      b) a U shape;
      c) an S shape; and
      d) an elongated shape.

10. The modular magnet assembly of claim 1, wherein magnets are enveloped in a jacket with a spring made of resilient and biocompatible material on either side of the jacket.

11. The modular magnet assembly of claim 10, wherein
    (i) the jacket is a shape memory material;
    (ii) during delivery, the modular magnet assembly automatically assumes a configuration;
    (iii) the jacket has a passageway sized to receive a wire guide; or
    (iv) a deployment configuration of the modular magnet assembly is a circular shape.

12. The modular magnet assembly of claim 1, wherein magnets from the first set of modular magnets and magnets from the second set of modular magnets are composed of a chain of ring-shaped magnetic elements linked to each other by a network of mechanical elements.

13. The modular magnet assembly of claim 12, wherein
    (i) the magnets are enveloped with a network of sheets;
    (ii) alternate and specific geometry ease the articulation between magnets; or
    (iii) magnets and the network of sheets are linked together through a centralized axis.

14. The modular magnet assembly of claim 1 and means comprising
    laparoscopic trocars; or
    endoscopy means.

15. The modular magnet assembly of claim 1, wherein magnets from the first set of modular magnets and from the second set of modular magnets, when in proximity to one another, are in a configuration of (North-South-North-South)/(South-North-South-North).

* * * * *